United States Patent [19]
Sakurai et al.

[11] Patent Number: 6,150,547
[45] Date of Patent: Nov. 21, 2000

[54] IRON-CASEIN COMPLEX HYDROLYZATE AND PROCESS FOR THE PRODUCTION THEREOF

[75] Inventors: Toshio Sakurai, Tokyo; Akihito Ikenaga, Saitama; Taishi Oda, Tokyo; Toshiaki Uchida, Saitama; Akira Tomizawa, Saitama; Hitoshi Aikawa, Saitama; Ken Takahashi, Hokkaido, all of Japan

[73] Assignee: Snow Brand Milk Products Co., Ltd., Sappore, Japan

[21] Appl. No.: 09/194,170

[22] PCT Filed: Mar. 20, 1998

[86] PCT No.: PCT/JP98/01222

§ 371 Date: Jan. 25, 1999

§ 102(e) Date: Jan. 25, 1999

[87] PCT Pub. No.: WO98/42862

PCT Pub. Date: Oct. 1, 1998

[30] Foreign Application Priority Data

Mar. 21, 1997 [JP] Japan .................................. 9-087378

[51] Int. Cl.$^7$ .............................. C07F 15/02; C07K 14/00
[52] U.S. Cl. .......................... 556/148; 530/400; 514/502; 514/6; 426/74
[58] Field of Search .......................... 530/400; 556/148; 514/6, 502

[56] References Cited

U.S. PATENT DOCUMENTS

| 2,849,334 | 8/1958 | Hart | 117/64 |
| 2,945,783 | 7/1960 | Beekman et al. | 167/55 |
| 4,172,072 | 10/1979 | Ashmead | 260/115 |

*Primary Examiner*—Porfirio Nazario-Gonzalez
*Attorney, Agent, or Firm*—Burgess, Ryan & Wayne

[57] ABSTRACT

This invention provides carbonic acid- and/or hydrogencarbonic acid-iron-hydrolyzates of casein complexes containing a large amount of iron, without causing precipitation after heating their aqueous solution or astringent taste and the processes for production thereof. The complexes of the present invention are prepared by (1) partial hydrolysis of carbonic acid- and/or hydrogencarbonic acid-iron-casein complexes with a protease or (2) mixing carbonic acid and/or hydrogencarbonic acid, iron and partial hydrolyzates of casein with a protease. These complexes are used favorably as food additives, raw materials of medicines or feed components due to their lack of precipitation by heating their aqueous solution, or astringent taste.

5 Claims, 4 Drawing Sheets

IRON-CASEIN COMPLEX HYDROLYZATE AND PROCESS FOR THE PRODUCTION THEREOF

FIELD OF THE INVENTION

This invention relates to carbonic acid- and/or hydrogencarbonic acid-iron-hydrolyzates of casein complexes. Furthermore, this invention relates to processes for the preparation of carbonic acid- and/or hydrogencarbonic acid-iron-hydrolyzates of casein complexes.

The carbonic acid- and/or hydrogencarbonic acid-iron-hydrolyzates of casein complexes of the present invention have characteristic features of thermoresistance or thermostability without exhibiting iron characteristic astringent taste after heat sterilization and can exist in aqueous solution. Thus, the compounds of the present invention are useful as raw materials of foods and drinks, medicines and feeds for prevention and treatment of anemia, and reinforcement of iron content in the body. Furthermore, the carbonic acid- and/or hydrogencarbonic acid-iron-hydrolyzates of casein complexes of the present invention have advantages that they exhibit favorable taste and can be handled easily in the production procedure without loss of the solid content because they do not aggregate in aqueous solution.

BACKGROUND OF THE INVENTION

The iron uptake of Japanese has been maintained at about 100% sufficiency without change since 1975, and iron as a nutrient in meals must be taken up with care. In the world, iron is considered as a nutrient which is often liable to be deficient, particularly the supply of iron in enriched foods and medicines for persons with anemic tendency, and pregnant and nursing females. However, addition of an iron salt such as iron sulfate or citrate as an iron reinforcing agent in foods and drinks has drawbacks since it cause problems of characteristic astringent taste when added in foods and drinks and injury to gastrointestinal mucosa, thus the amount of addition is limited. Furthermore, an organic iron compound, heme iron, causes problems in taste such as metallic or fishy taste and its addition to foods is highly limited.

Addition of milk casein, amino acid or casein phosphopeptide has been tried for the improved absorption of iron [Japanese Laid-open Patent Application No. 162843 (1984)]. However, these methods could not diminish characteristic astringent taste of iron without reducing the amount of its addition.

The inventors of the present invention developed a method to reduce the characteristic astringent taste of iron by binding iron with casein [Japanese Laid-open Patent Application No. 83400 (1990)]. However, the iron casein prepared by binding iron with casein is devoid of thermostability and shows characteristic astringent taste of iron by thermal pasteurization at 90° C. for 10 minutes, 120° C. for 2–3 seconds or retort pasteurization. This was considered to be caused by release of iron from casein due to weak binding of iron and casein, and formation of iron hydroxides or the like.

Then, the inventors of the present invention further investigated and found that the binding of iron and casein can be reinforced by using carbonic acid and/or hydrogencarbonic acid and succeeded to get carbonic acid- and/or hydrogencarbonic acid-iron-casein complexes [Japanese Laid-open Patent Application No. 259572 (1995)]. The carbonic acid- and/or hydrogencarbonic acid-iron-casein complexes are thermoresistant without showing iron characteristic astringent taste even by heat sterilization and are useful as raw materials of foods and drinks, medicines, feeds and so forth for prevention and treatment of anemia and reinforcement of iron content. However, the carbonic acid- and/or hydrogencarbonic acid-iron-casein complexes had drawbacks of tendency to aggregate by dissolution in water, difficult to treat in the production procedure and liable to lose solid mass. Furthermore, their sandy taste remains to be solved.

The inventors of the present invention actively investigated methods to solve the above mentioned drawbacks of carbonic acid- and/or hydrogencarbonic acid-iron-casein complexes, and found that carbonic acid- and/or hydrogencarbonic acid-iron-partial hydrolyzates of casein complexes prepared by hydrolysis of carbonic acid- and/or hydrogencarbonic acid-iron-casein complexes with a protease, or by hydrolysis of casein with a protease to give partial hydrolyzates of casein followed by preparation of carbonic acid- and/or hydrogencarbonic acid-iron-partial hydrolyzates of casein complexes provides thermoresistant, stable to heat sterilization products without iron characteristic astringent taste or aggregation by dissolution in water and accomplished the present invention. Therefore, one object of the present invention is to provide carbonic acid- and/or hydrogencarbonic acid-iron-partial hydrolyzates of casein complexes having characteristic features of thermoresistant, stability to heat sterilization without iron characteristic astringent taste or aggregation by dissolution in water. In addition, the present invention provides processes for the preparation of carbonic acid- and/or hydrogencarbonic acid-iron-partial hydrolyzates of casein complexes.

DESCRIPTION OF THE PRESENT INVENTION

The present invention is proposed to solve aforementioned problems and relates to carbonic acid- and/or hydrogencarbonic acid-iron-partial hydrolyzates of casein complexes containing 1–1,000 atoms of iron and one or more molecule of carbonic acid and/or hydrogencarbonic acid per one molecule of casein prior to the hydrolysis. The solubility of the dried powder of complexes in water is at least 15% without aggregation or precipitation even after heating at 90° C. for 10 minutes, and the solution is free of iron characteristic astringent taste.

The above mentioned complexes of the present invention are thermoresistant without showing iron characteristic astringent taste by heat sterilization, aggregation in aqueous solution or precipitation by heating at 90° C. for 10 minutes.

The carbonic acid- and/or hydrogencarbonic acid-iron-partial hydrolyzates of casein complexes can be prepared by the following two procedures.

That is, the first procedure is formation of carbonic acid- and/or hydrogencarbonic acid-iron-casein complexes, followed by partial hydrolysis of casein with a protease.

The carbonic acid- and/or hydrogencarbonic acid-iron-casein complexes used in the procedure can be prepared by 1) simultaneous mixing of solution containing a carbonic acid, a hydrogencarbonic acid, or a carbonic acid and a hydrogencarbonic acid (solution A), a solution containing iron (solution B) and a solution containing casein (solution C), 2) mixing a carbonic acid, hydrogencarbonic acid, or a carbonic acid and/or a hydrogencarbonic acid solution (solution A), and a solution containing iron and casein (solution B), or 3) mixing a solution containing a carbonic acid, a hydrogencarbonic acid, or a carbonic acid and a hydrogencarbonic acid, and casein (solution A) and an iron containing solution (solution B).

In the process 1), the molar concentration of iron ion in solution B is made ⅓ or less to those of a carbonic acid and a hydrogencarbonic acid ions dissolved in a mixed solution of A, B and C. The molar concentration of casein in solution C is adjusted to 1¹/1,000 to that of iron ion in solution B. In the process 2), the molar concentration of iron ion in solution B is made ⅓ or less to those of a carbonic acid and a hydrogencarbonic acid ions in a mixture of solutions A and B, and the molar number of casein in solution B is adjusted to 1¹/1,000 to that of iron ion in solution B.

In addition, in the process 3), the molar concentration of iron ion in solution B is made ⅓ or less to those of a carbonic acid and a hydrogencarbonic acid ions in a mixed solutions A and B, and the molar number of casein in solution A is adjusted to 1¹/1,000 to that of iron ion in solution A.

The second procedure is a process of partial hydrolysis of casein with a protease in advance to give partial hydrolyzates of casein, and to give carbonic acid- and/or hydrogencarbonic acid-iron-partial hydrolyzates of casein complexes from the partial hydrolyzates of casein. In other words, carbonic acid- and/or hydrogencarbonic acid-iron-partial hydrolyzates of casein complexes are obtained by mixing i) a carbonic acid, a hydrogencarbonic acid, or a carbonic acid and a hydrogencarbonic acid, ii) iron, and iii) casein partial hydrolyzates prepared by partial hydrolysis of casein with a protease to react to form carbonic acid- and/or hydrogencarbonic acid-iron-partial hydrolyzates of casein complexes.

In the above mentioned second procedure, mixing of the aforementioned three components can be carried out by the following methods, that is:

1) Simultaneous mixing of solution containing a carbonic acid, a hydrogencarbonic acid, or a carbonic acid and a hydrogencarbonic acid (solution A), a solution containing iron (solution B), and a solution of partial hydrolyzates of casein solution (solution C).

2) Mixing of solution containing a carbonic acid, a hydrogencarbonic acid, or a carbonic acid and a hydrogencarbonic acid (solution A) and a solution containing iron and a partial hydrolyzate of casein prepared by partial hydrolysis of casein with a protease (solution B).

3) Mixing of a solution containing a partial hydrolyzate of casein prepared by partial hydrolysis of casein with a protease and a carbonic acid, a hydrogencarbonic acid, or a carbonic acid and a hydrogencarbonic acid (solution A) and a solution containing iron (solution B).

In the procedure 1), the molar concentration of iron ion in solution B is made ⅓ or less to those of a carbonic acid and a hydrogencarbonic acid ions dissolved in a mixed solution of A, B and C, and molar number of partial hydrolyzates of casein in solution C is adjusted to 1¹/1,000 molar number of iron ion in solution B calculated as casein before partial hydrolysis.

In the procedure 2), the molar concentration of iron ion in solution B is made ⅓ or less to those of a carbonic acid and a hydrogencarbonic acid ions dissolved in a mixed solution of A and B, and the molar number of hydrolyzates of casein in solution B is adjusted to 1¹/1,000 to that of iron ion in solution B calculated as casein before hydrolysis.

Further, in the procedure 3), the molar concentration of iron ion in solution B is made ⅓ or less to those of a carbonic acid and a hydrogencarbonic acid ions dissolved in a mixed solution of A and B, and the molar number of casein partial hydrolyzed product in solution A is adjusted to 1¹/1,000 to that of iron ion in solution B calculated as casein before partial hydrolysis.

Thus, the carbonic acid- and/or hydrogencarbonic acid-iron-partial hydrolyzates of casein complexes can be prepared to give following properties of 1) to 4).

1) The complexes contain 1–1,000 atoms of iron and one or more molecule of a carbonic acid and/or a hydrogencarbonic acid per one molecule of casein prior to the hydrolysis, 2) the dried powder of complexes dissolves in water to give at least 15% solution, 3) the aqueous solution gives no precipitate by heating at 90° C. for 10 minutes, and 4) the solution gives no iron characteristic astringent taste.

The carbonic acid- and/or hydrogencarbonic acid-iron-partial hydrolyzates of casein complexes of the present invention do not form precipitates in the aqueous solution after heating at 90° C. for 10 minutes, and this thermoresistance is derived from the use of partially and enzymically hydrolyzates of casein as a raw material. The enzymic hydrolysis is preferably carried out with a protease to give partial hydrolyzates, no more than 55% of which is a hydrolyzate with molecular weight of 15,000 or more and no more than 34% of which is that with molecular weight of less than 800.

BEAT MODE FOR CARRYING OUT THE PRESENT INVENTION

The present invention is practically explained at first by processes for preparation of the complexes.

The first processes composed of preparation of carbonic acid- and/or a hydrogencarbonic acid-iron-casein complex, followed by partial hydrolysis of the carbonic acid- and/or hydrogencarbonic acid-iron-casein complex with a protease to give carbonic acid and/or hydrogencarbonic acid-iron-partial hydrolyzates of casein complex are explained.

The processes have following three variations of (1) to (3).

(1) Simultaneous mixing of solution containing a carbonic acid, a hydrogencarbonic acid, or a carbonic acid and a hydrogencarbonic acid (solution A), a solution containing iron (solution B), and a solution containing casein (solution C) to give a carbonic acid- and/or hydrogencarbonic acid-iron-casein complex. However, the molar concentration of iron ion in solution B is made ⅓ or less to those of a carbonic acid and a hydrogencarbonic acid ions dissolved in a mixed solution of A, B and C. The molar number of casein in solution C is adjusted to 1¹/1,000 to that of iron ion in solution B. The carbonic acid- and/or hydrogencarbonic acid-iron-casein complex is partially hydrolyzed with a protease to give the carbonic acid- and/or hydrogencarbonic acid-iron-partial hydrolyzates of casein complex of the present invention.

(2) Mixing of solution containing a carbonic acid, a hydrogencarbonic acid, or a carbonic acid and a hydrogencarbonic acid (solution A), and a solution containing iron and casein (solution B) to give the complex of carbonic acid- and/or hydrogencarbonic acid-iron-casein complex. However, the molar concentration of iron ion in solution B is made ⅓ or less of those of a carbonic acid and a hydrogencarbonic acid ions dissolved in a mixed solution of A and B, and the molar number of casein in solution B is adjusted to 1¹/1,000 to that of iron ion in solution B. The carbonic acid- and/or hydrogencarbonic acid-iron-casein complex is partially hydrolyzed with a protease to give the carbonic acid- and/or hydrogencarbonic acid-iron-partial hydrolyzates of casein complex of the present invention.

(3) Mixing of a carbonic acid, a hydrogencarbonic acid, or a carbonic acid and a hydrogencarbonic acid, and casein solution (solution A), and a solution containing iron (solution B) to give the complex of carbonic acid- and/or hydrogencarbonic acid-iron-casein complex. However, the molar concentration of iron ion in solution B is made ⅓ or less of those of a carbonic acid and a hydrogencarbonic acid ions dissolved in a mixed solution of A and B, and the molar number of casein in solution A is adjusted to 1-¹⁄₁,₀₀₀ to that of iron ion in solution B. The carbonic acid- and/or hydrogencarbonic acid-iron-casein complex is partially hydrolyzed with a protease to give the carbonic acid- and/or hydrogencarbonic acid-iron-partial hydrolyzates of casein complex of the present invention.

In the second method, that is the procedures for the production of carbonic acid- and/or hydrogencarbonic acid-iron-partial hydrolyzates of casein complex from partial hydrolyzates of casein prepared by partial hydrolysis of casein with a protease in advance include the following (1) to (3) variations:

(1) Simultaneous mixing of solution containing a carbonic acid, a hydrogencarbonic acid, or a carbonic acid and a hydrogencarbonic acid (solution A), a solution containing iron (solution B), and a solution of partial hydrolyzates of casein solution (solution C) using hydrolyzates of casein prepared by partial hydrolysis of casein with a protease in advance to give carbonic acid-and/or hydrogencarbonic acid-iron-partial hydrolyzates of casein complex of the present invention. However, the molar concentration of iron ion in solution B is made ⅓ or less of those of a carbonic acid and a hydrogencarbonic acid ions dissolved in a mixed solution of A, B and C, and molar number of partial hydrolyzates of casein in solution C is adjusted to 1-¹⁄₁,₀₀₀ molar number of iron ion in solution B calculated as casein before partial hydrolysis.

(2) Mixing of solution containing a carbonic acid, a hydrogencarbonic acid, or a carbonic acid and a hydrogencarbonic acid (solution A) and a solution containing iron and a partial hydrolyzate of casein (solution B) using hydrolyzates of casein prepared by partial hydrolysis of casein with a protease in advance to give a carbonic acid- and/or hydrogencarbonic acid-iron-partial hydrolyzates of casein complex. However, the molar concentration of iron ion in solution B is made ⅓ or less of those of a carbonic acid and a hydrogencarbonic acid ions dissolved in a mixed solution of A and B. The molar number of partial hydrolyzates of casein in solution B is adjusted to 1-¹⁄₁,₀₀₀ molar number of iron ion in solution B calculated as casein before hydrolysis.

(3) Mixing of a carbonic acid, a hydrogencarbonic acid, or a carbonic acid and a hydrogencarbonic acid, and partial hydrolyzates of casein solution prepared by partial hydrolysis of casein with a protease in advance (solution A) and a solution containing iron (solution B) to give a carbonic acid-and/or hydrogencarbonic acid-iron-partial hydrolyzates of casein complex. However, the molar concentration of iron ion in solution B is made ⅓ or less of those of a carbonic acid and a hydrogencarbonic acid ions dissolved in a mixed solution of A and B. The molar number of partial hydrolyzates of casein in solution A is adjusted to 1-¹⁄₁,₀₀₀ molar number of iron ion in solution B calculated as casein before hydrolysis.

In the present invention, a carbonic acid and/or a hydrogencarbonic acid used for the preparation of a carbonic acid- and/or a hydrogencarbonic acid-iron-casein complex, or a carbonic acid- and/or a hydrogencarbonic acid-iron-partial hydrolyzates of casein complex may be used in forms of acids or water soluble salts. Iron is generally used in the form of a water soluble salt.

The carbonic acid and/or hydrogencarbonic acid, iron, and casein or partial hydrolyzates of casein may be used in the form of solution or solid such as salts for the preparation of a carbonic acid- and/or a hydrogencarbonic acid-iron-casein complex, or a carbonic acid- and/or a hydrogencarbonic acid-iron-partial hydrolyzates of casein complex. Solid state carbonates and/or hydrogencarbonates, iron, and casein or partial hydrolyzates of casein may be simultaneously dissolved and used. However, procedure that would lead to the formation of a solution solely containing carbonates and/or hydrogencarbonates, and iron must be avoided.

The casein used in the present invention may be illustrated, for example, as casein, acidic casein, casein sodium, lactic casein, α-casein, β-casein and κ-casein isolated from milk of mammals such as human being and cattle. These casein are commercially available or as methods to massively isolate them are known, products produced by these methods may also be used. In addition, those produced by microorganisms, animal cells and transgenic animals using gene technology may also be used. When crude casein such as mixtures of α-casein, β-casein and κ-casein is used as a raw material, the molar concentration of casein in the solution is estimated from average molecular weight based on the ratios of the components The carbonic acid and/or hydrogencarbonic acid used in the present invention may be illustrated as carbonated water, ammonium hydrogencarbonate, sodium hydrogencarbonate, potassium hydrogen-carbonate, sodium carbonate, calcium carbonate and so forth. As iron compounds, water soluble iron salts such as ferric chloride and ferric sulfate may be used. As pH adjusting agents, sodium hydroxide, ammonia, potassium hydroxide, hydrochloric acid, citric acid and lactic acid may simultaneously be used. The pH of the reaction mixture is generally adjusted to 2–9.

In the present invention, proteases used for partial hydrolysis of carbonic acid- and/or hydrogencarbonic acid-iron-casein complex or those used for partial hydrolysis of casein may be illustrated for example as animal derived pepsin, trypsin, chymotrypsin chymosin and pancreatin, and plant derived papain. In addition, proteases derived from microorganisms or those prepared by gene recombinant technology may also be used.

In addition, the solubility of carbonic acid- and/or hydrogencarbonic acid-iron-partial hydrolyzates of casein complex largely vary with the molecular weight distribution of partial hydrolyzates of casein in the complex. Thus, the reaction conditions for partial hydrolysis with protease must be investigated prior to the hydrolysis. In this connection, the molecular weight distribution of hydrolyzates of casein in the carbonic acid- and/or hydrogencarbonic acid-iron-partial hydrolyzates of casein complex is preferably no more than 55% for the hydrolyzates of casein having molecular weight of 15,000 or more, and no more than 34% for that having molecular weight of less than 800. Further, preferably, more than 20% of partial hydrolyzates of casein has molecular weight of 800–15,000 and most preferably more than 50%. Therefore, the partial hydrolysis of casein in the present invention means hydrolysis of casein to give partial hydrolyzates of casein, no more than 55% of which is a hydrolyzate with molecular weight of 15,000 or more and no more than 34% of which is that with molecular weight of less than 800.

Figure 1:
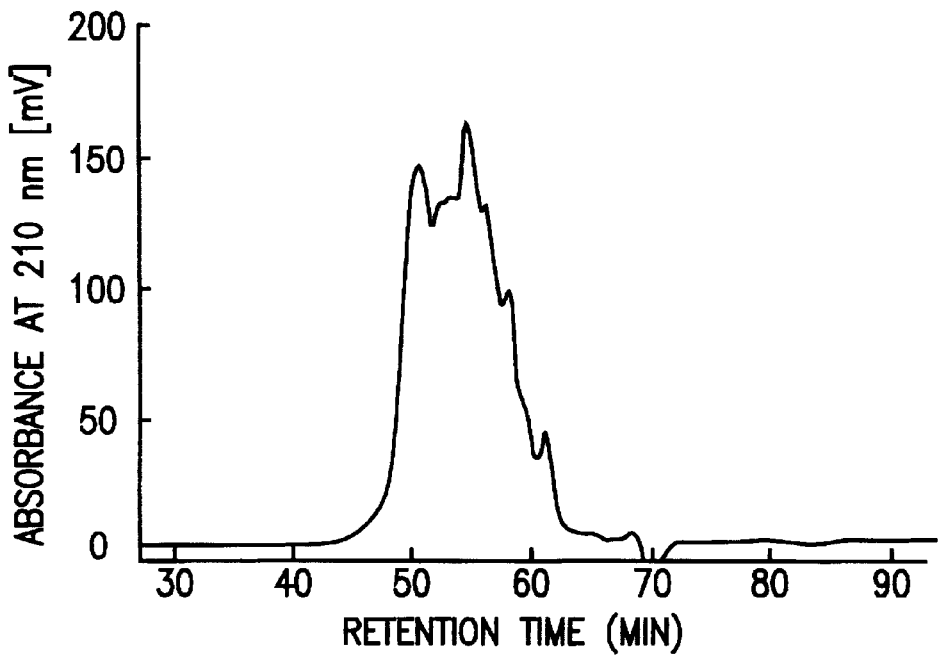
FIG. 1 shows a molecular weight distribution of partial hydrolyzates of lactic casein obtained by Example 3.

The present invention will be practically explained by the following examples. These examples are shown merely as illustration and not to be constructed to limit the scope of the present invention.

EXAMPLE 1

(Solution A) One liter of an aqueous solution of 1,200 mmol sodium hydrogencarbonate.

(Solution B) 0.2 L of an aqueous solution of ferric chloride containing 10mmol of iron.

(Solution C) 0.8 L of an aqueous solution of 0.1 mmol lactic casein (Dairy Board, New Zealand).

However, adjustment of molar concentration was carried out with average molecular weight. The average molecular weight was estimated from respective theoretical molecular weight and composition ratio of α-casein, β-casein and κ-casein determined by urea-sodium dodecylsulfate (SDS)-electrophoresis.

Solution B (0.2 L) and solution C (0.8 L) were mixed to give solution (B+C) (1 L), then the mixed solution (B+C) (1 L) was added to solution A (1 L) to give a hydrogencarbonic acid-iron-casein complex. The solution containing the complex was desalted by treatment with an ultrafiltration membrane of 5,000 molecular weight cut, concentrated to make casein concentration up to 5% in the complex, and adjusted to pH 8.0 by adding sodium hydrogencarbonate. In the reaction solution, 1,200 U of protease, trypsin (PTN6.0S: Novo Nordisk)/g casein was added, sodium hydroxide was added to maintain the solution at pH 8.0 and partial hydrolysis of casein was carried out at 50° C. The partial hydrolysis was performed till the reaction solution became clear with gross observation. The temperature of the reaction mixture was kept at 85° C. for 20 minutes to inactivate the enzyme and to terminate the reaction. The partial hydrolysis of casein required about 7 hrs. The reaction solution was dialyzed and lyophilized to give 3.0 g of hydrogencarbonic acid-iron-partial hydrolyzates of casein complex.

The solubility of the hydrogencarbonic acid-iron-partial hydrolyzates of casein complex was examined by dissolving the complex in a simulated liquid food buffer containing 0.05 moll imidazole and 0.15 moll sodium chloride (hereinafter referred as a simulated buffer), up to give 15% solution. Thus, the hydrogencarbonic acid-iron-partial hydrolyzates of casein complex completely dissolved without becoming turbid or forming aggregation.

The shelf life of the above mentioned hydrogencarbonic acid-iron-partial hydrolyzates of casein complex was examined in a simulated buffer prepared by dissolving the complex. The simulated buffer solution containing the complex was diluted to give iron concentration of 3.6 mmol, heat sterilized at 90° C. for 10 minutes and kept at 5° C. No precipitation was found even after six month storage.

EXAMPLE 2

(Solution A) One liter of an aqueous solution of 1,200 mmol sodium hydrogencarbonate.

(Solution B) 0.2 L of an aqueous solution of 9 mmol ferric sulfate containing 9 mmol of iron, (Solution C) 0.8 L of an aqueous solution of 0.1 mmol lactic casein (Sigma Chemical Co.).

Their molar concentrations were adjusted in a similar manner with that of Example 1.

Solution B (0.2 L) and solution C (0.8 L) were mixed to give solution (B+C) (1 L), and then the mixed solution (B+C) (1 L) was added to solution A (1 L) to give a hydrogencarbonic acid-iron-casein complex. The solution containing the complex was desalted by treatment with an ultrafiltration membrane of 5,000 molecular weight cut, concentrated to make casein concentration up to 5% in the complex, and adjusted to pH 8.0 by adding sodium hydrogencarbonate In the reaction solution, 600 U of protease, papain (W-40: Amano Pharmaceutical Co., Ltd.)/g casein was added, sodium hydroxide was added to maintain the solution at pH 8.0 and partial hydrolysis of casein was carried out at 65° C. The partial hydrolysis was performed till the reaction solution became clear with gross observation. The reaction mixture was kept at 85° C. for 20 minutes to inactivate the enzyme and to terminate the reaction. The partial hydrolysis required about 6 hrs. The reaction solution was dialyzed and lyophilized to give 2.4 g of hydrogencarbonic acid-iron-partial hydrolyzates of casein complex.

The solubility of the hydrogencarbonic acid-iron-partial hydrolyzates of casein complex was examined by a similar manner with that of Example 1. Thus, the hydrogencarbonic acid-iron-partial hydrolyzates of casein complex completely dissolved without becoming turbid or forming aggregation.

The shelf life of the above mentioned hydrogencarbonic acid-iron-partial hydrolyzates of casein complex was examined in a similar manner with that of Example 1. No precipitation was found even after six months storage.

TEST EXAMPLE 1

A sensory evaluation test was carried out for simulated buffer solutions prepared by dissolution of hydrogencarbonic acid-iron-partial hydrolyzates of casein complexes of Examples 1 and 2. That is, 10 male and 10 female panelists were given the simulated buffer solutions containing hydrogencarbonic acid-iron-partial hydrolyzates of casein complex of Example 1 or 2 and asked whether they felt astringent taste or not. A blind-fold was given to each panelist to avoid the influence of appearance to the judgment. Test for one sample was carried out in an order of the control first and then the sample, and at least one day interval was placed prior to the test of the next sample. Furthermore, the test samples were given randomly to each panelist to avoid the deviation between test days for evaluation of sample. Similar sensory evaluation test was performed using solution of ferrous sulfate having iron concentration of 3.6 mmol, which was expected to exhibit astringent taste. The number of panelists who sensed astringent taste is shown in Table 1.

TABLE 1

| Sample | Number of panelist who sensed astringent taste |
|---|---|
| Example 1 | 0/20 |
| Example 2 | 0/20 |
| Ferrous sulfate | 20/20 |

As shown in Table 1, the hydrogencarbonic acid-iron-partial hydrolyzates of casein complex of Example 1 or 2 has no characteristic astringent taste peculiar to iron.

EXAMPLE 3

(Solution A) One liter of an aqueous solution of 1,200 mmol sodium hydrogencarbonate.

(Solution B) 0.2 L of an aqueous solution of ferric chloride containing 10 mmol of iron.

(Solution C) 0.8 L of an aqueous solution of 0.1 mmol lactic casein calculated as casein before the partial hydrolysis.

The molar concentration was adjusted in a similar manner with that of Example 1.

The partial hydrolyzates of lactic casein used for the preparation of solution C was prepared as shown below. That is, lactic casein (Dairy Board, New Zealand) was dissolved to give 5% reaction solution and sodium hydrogencarbonate was added to adjust the solution at pH 8.0. A protease, trypsin (PTN6.0S: Novo Nordisk), was added at a ratio of 1,000 U/g of casein and partially hydrolyzed at 50° C. for five hours while maintaining the solution at pH 8.0 by adding sodium hydroxide. The reaction solution was kept at 85° C. for 20 minutes to inactivate the enzymic activity and to terminate the partial hydrolysis. The reaction solution was lyophilized to give 3.1 g of partial hydrolyzates of lactic casein.

The molecular weight of the partial hydrolyzates of lactic casein was determined with a gel filtration chromatography. That is, a solution of the partial hydrolyzates of lactic casein was made to flow through a high performance liquid chromatography (HPLC) packed with TSKgel 3000PWxl (300× 7.8 mm: Tosoh Corp.) and eluted with a 55% acetonitrile containing 0.1% trifluoroacetic acid at a rate of 0.3 ml/minute. The absorbance of elute at 210 nm was determined. Similar procedure was carried out using standard protein and peptide with known molecular weights and the elution time was determined, respectively. The molecular weight and elution time of the standard protein and peptide are shown in Table 2.

TABLE 2

| | Molecular weight | Elution time |
|---|---|---|
| αs-Casein | 23,000 | 39.8 (minutes) |
| β-Casein | 24,000 | 40.0 |
| Aprotinin | 6,500 | 48.8 |
| Insulin B chain | 3,496 | 51.8 |
| Insulin A chain | 2,532 | 55.2 |
| Angiotensin II | 1,046 | 58.7 |
| Glutathione | 307 | 64.2 |

Molecular weight distribution of partial hydrolyzates of lactic casein was estimated from integrated value of absorbance and elution time in referring to the molecular weight and elution time of the standard protein and peptide. The results are shown in FIG. 1. The Figure shows that partial hydrolyzates of lactic casein having molecular weight of 800–15,000 consists 94% of the total product, Above mentioned solution B (0.2 L) and solution C (0.8 L) were mixed to give solution (B+C) (1 L) and the resultant solution (B+C) (1 L) was added to solution A (1 L) to give hydrogencarbonic acid-iron-partial hydrolyzates of casein complex. A solution containing the complex e was dialyzed and lyophilized to give 2.7 g of hydrogencarbonic acid-iron-partial hydrolyzates of casein complex. The diffusate of a solution containing hydrogencarbonic acid-iron-partial hydrolyzates of casein complex was concentrated with an evaporator, however no iron content was detected by determination with an emission spectrophotometer (ICP). Therefore, all iron is considered to be used as a component of hydrogencarbonic acid-iron-partial hydrolyzates of casein complex.

The solubility of the above hydrogencarbonic acid-iron-partial hydrolyzates of casein complex was determined in a similar manner with that of example 1 and found that the complex completely dissolves without forming coagulation or becoming turbid. The shelf life of a simulated buffer solution containing the above hydrogencarbonic acid-iron-partial hydrolyzates of casein complex was determined in a similar manner with that of Example 1 and it was found that the buffered solution shows no precipitation even after storage for six months.

EXAMPLE 4

In a 5% aqueous solution of lactic casein (Dairy Board, New Zealand) at a concentration of 5%, sodium hydrogencarbonate was added to adjust the pH at 0.0. In the reaction solution, a protease, papain (w-40: Amano Pharmaceutical Co., Ltd.) was added at a ratio of 10 U/q of casein and the partial hydrolysis was carried out at 65° C. for three hours while maintaining pH at 8.0 by adding sodium hydroxide. Thereafter, the reaction solution was kept at 85° C. for 20 minutes to inactivate the enzyme activity and terminate the reaction. The treated reaction solution was lyophilized to give 3.4 g of hydrolyzates of lactic casein.

Figure 2:
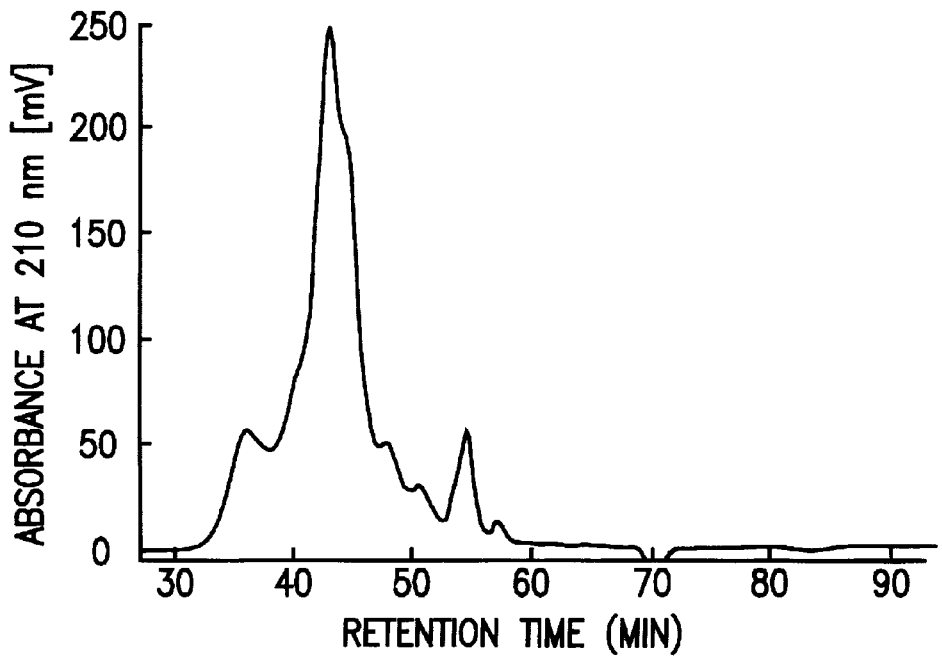
FIG. 2 shows a molecular weight distribution of partial hydrolyzates of lactic casein obtained by Example 4.

The molecular weight distribution of the hydrolyzates of lactic casein was determined in a similar manner with that of Example 3 and the result is shown in FIG. 2. The Figure shows that hydrolyzates of lactic casein having molecular weight of 800–15,000 consists 45% of the total product and the rests have molecular weight of over 15,000.

A hydrogencarbonic acid-iron-partial hydrolyzates of casein complex was prepared in a similar manner with that of Example 3 using the above mentioned hydrolyzates of lactic casein complex. The concentration of iron in diffusate of a solution containing the hydrogencarbonic acid-iron-partial hydrolyzates of casein complex was determined in a similar manner with that of Example 3 and no iron was detected. Therefore, all iron is considered to be used as a component of hydrogencarbonic acid-iron-partial hydrolyzates of casein complex.

The shelf life of a simulated buffer solution containing the above hydrogencarbonic acid-iron-partial hydrolyzates of casein complex was determined in a similar manner with that of Example 1 and it was found that the buffered solution shows no precipitation even after storage for six months.

EXAMPLE 5

In a 5% solution of lactic casein (Dairy Board, New Zealand), sodium hydrogencarbonate was added to make pH 8.0. In the reaction solution, a protease, bromelain F (Amano Pharmaceutical Co., Ltd.) was added at a ratio of 1,000 U/g of casein and caused to partial hydrolysis at 65° C. for five hours while maintaining pH at 8.0 by adding sodium hydroxide. Thereafter, the reaction solution was kept at 85° C. for 20 minutes to inactivate the enzyme activity and terminate the reaction. The treated reaction solution was lyophilized to give 3.0 g of hydrolyzates of lactic casein.

Figure 3:
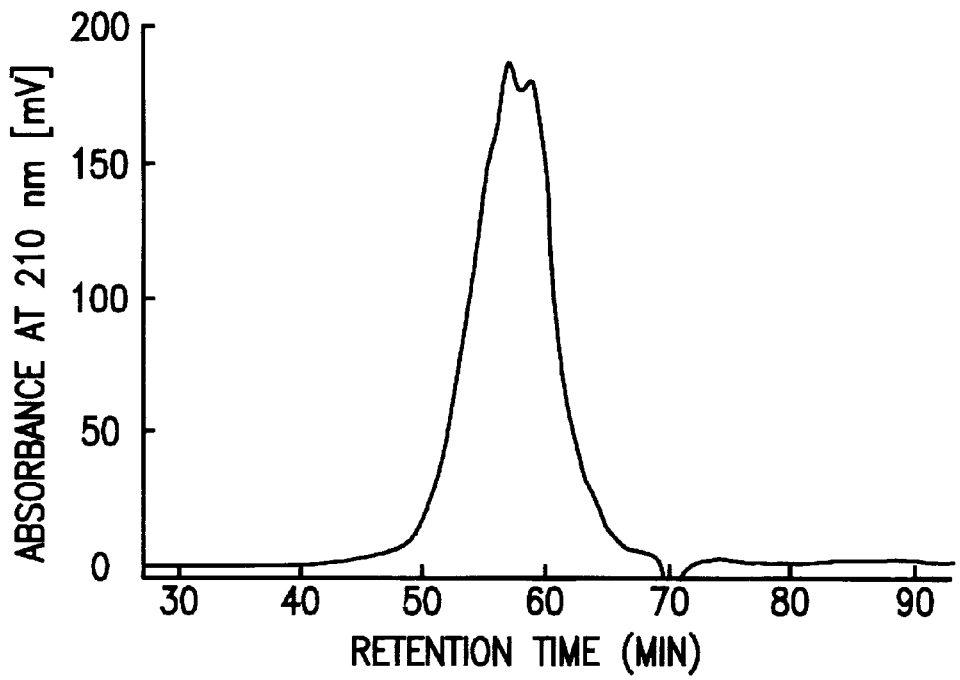
FIG. 3 shows a molecular weight distribution of partial hydrolyzates of lactic casein obtained by Example 5.

The molecular weight distribution of the hydrolyzates of lactic casein was determined in a similar manner with that of Example 3 and the result is shown in FIG. 3. The Figure shows that hydrolyzates of lactic casein having molecular weight of 800–15,000 consists 80% of the total product.

A hydrogencarbonic acid-iron-partial hydrolyzates of casein complex was prepared in a similar manner with that of Example 3 using the above hydrolyzate of lactic casein complex. The concentration of iron in diffusate of a solution containing the hydrogencarbonic acid-iron-partial hydrolyzates of casein complex was determined in a similar manner with that of Example 3 and no iron was detected. Therefore, all iron is considered to be used as a component of hydrogencarbonic acid-iron-partial hydrolyzates of casein complex.

The shelf life of a simulated buffer solution containing the above hydrogencarbonic acid-iron-partial hydrolyzates of casein complex was determined in a similar manner with that of Example 1 and it was found that the buffered solution shows no precipitation even after storage for six months.

EXAMPLE 6

In a 5% solution of lactic casein (Dairy Board, New Zealand), sodium hydrogencarbonate was added to added to adjust the pH at 8.0. In the reaction solution, a protease, protease P (Amano Pharmaceutical Co., Ltd.) was added at a ratio of 10 U/g of casein and the partial hydrolysis was carried out at 45° C. for five hours while maintaining pH at 8.0 by addition of sodium hydroxide. Thereafter, the reaction solution was kept at 85° C. for 20 minutes to inactivate the enzyme activity and terminate the reaction. The treated reaction solution was lyophilized to give 3.1 g of hydrolyzates of lactic casein.

Figure 4:
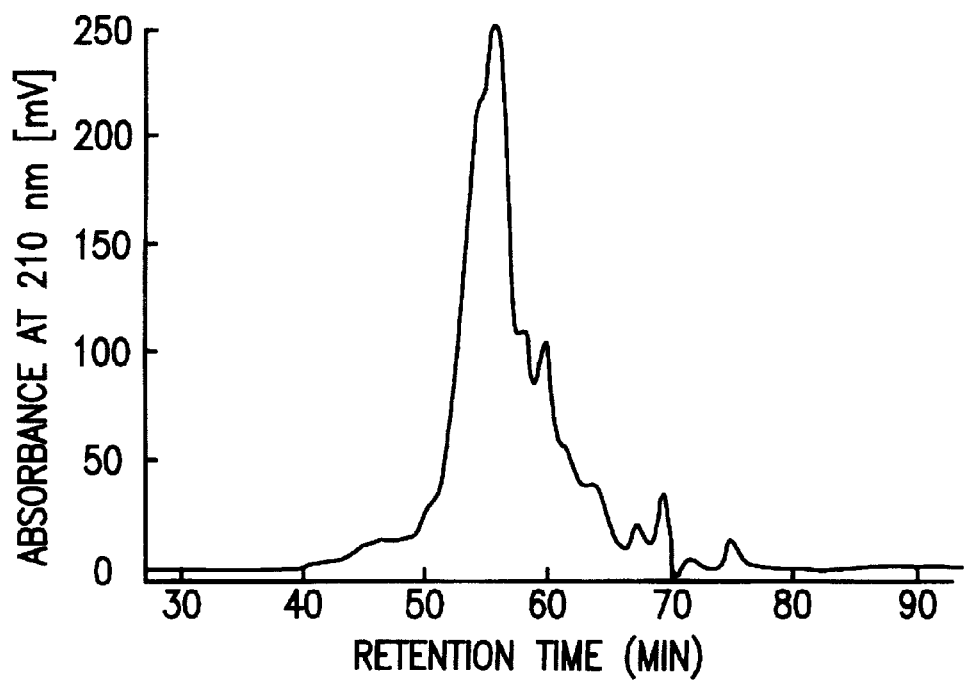
FIG. 4 shows a molecular weight distribution of partial hydrolyzates of lactic casein obtained by Example 6.

The molecular weight distribution of the hydrolyzates of lactic casein was determined in a similar manner with that of Example 3 and the result is shown in FIG. 4. The Figure shows that hydrolyzates of lactic casein having molecular weight of 800–15,000 consists 80% of the total product and those having molecular weight of over 15,000 consists 2% of the total product, and further those less than 800 consists 18% of the total product.

A hydrogencarbonic acid-iron-partial hydrolyzates of casein complex was prepared in a similar manner with that of Example 3 using the above mentioned hydrolyzates of lactic casein complex. The concentration of iron in diffusate of a solution containing hydrogencarbonic acid-iron-partial hydrolyzates of casein complex was determined in a similar manner with that of Example 3 and no iron was detected. Therefore, all iron is considered to be used as a component of hydrogencarbonic acid-iron-partial hydrolyzates of casein complex.

The shelf life of a simulated buffer solution containing the above mentioned hydrogencarbonic acid-iron-partial hydrolyzates of casein complex was determined in a similar manner with that of Example 1 and it was found that the buffered solution shows no precipitation even after storage for six months.

EXAMPLE 7

In a 5% solution of lactic casein (Dairy Board, New Zealand) sodium hydrogencarbonate was added to adjust the pH at 7.0. In the reaction solution, a protease, Fishase (Kaken Pharma Co., Ltd.) was added at a rate of 1,000 U/g of casein and the partial hydrolysis was carried out at 50° C. for one hour while maintaining pH at 7.0 by adding sodium hydroxide. Thereafter, the reaction solution was kept at 85° C. for 20 minutes to inactivate the enzyme activity and terminate the reaction. The treated reaction solution was lyophilized to give 2.8 g of hydrolyzates of lactic casein.

Figure 5:
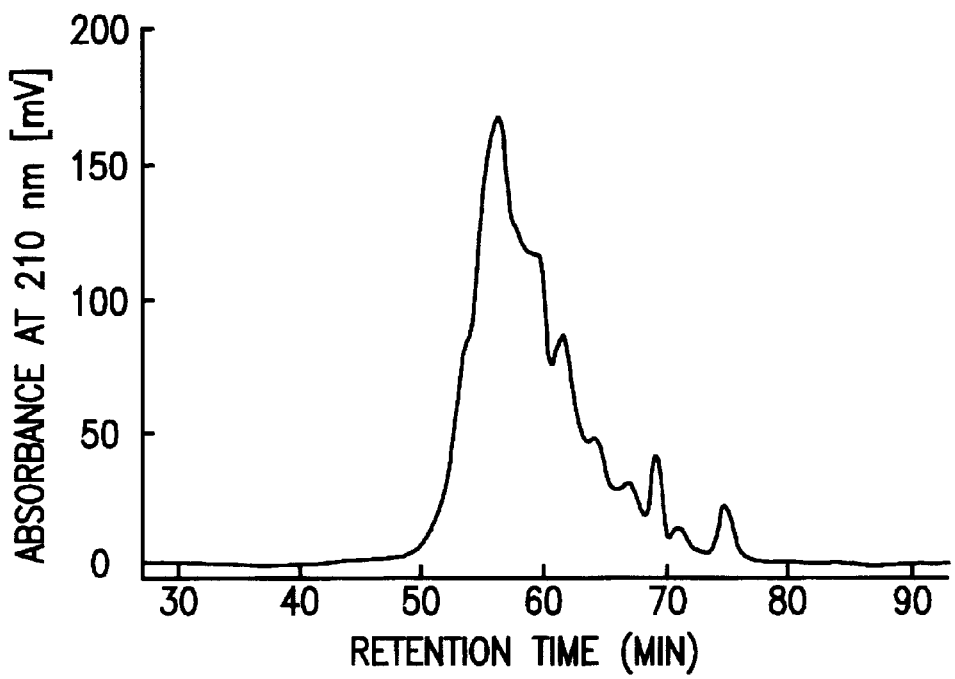
FIG. 5 shows a molecular weight distribution of partial hydrolyzates of lactic casein obtained by Example 7.

The molecular weight distribution of the hydrolyzates of lactic casein was determined in a similar manner with that of Example 3 and the result is shown in FIG. 5. The Figure shows that hydrolyzates of lactic casein having molecular weight of 800–15,000 consists 66% of the total product and the rests have molecular weight of less than 800.

A hydrogencarbonic acid-iron-partial hydrolyzates of casein complex was prepared in a similar manner with that of Example 3 using the above mentioned hydrolyzates of lactic casein. The concentration of iron in diffusate of a solution containing hydrogencarbonic acid-iron-partial hydrolyzates of casein complex was determined in a similar manner with that of Example 3 and no iron was detected. Therefore, all iron is considered to be used as a component of hydrogencarbonic acid-iron-partial hydrolyzates of casein complex.

The shelf life of a simulated buffer solution containing the above mentioned hydrogencarbonic acid-iron-partial hydrolyzates of casein complex was determined in a similar manner with that of Example 1 and it was found that the buffered solution shows almost no precipitation even after storage for six months.

TEST EXAMPLE 2

A sensory evaluation test was carried out for simulated buffer solutions of the hydrogencarbonic acid-iron-partial hydrolyzates of casein complexes of Examples 3–7. The sensory evaluation test was carried out in a similar manner with that of Test example 1. The number of panelists who sensed astringent taste is shown in Table 3.

TABLE 3

| Sample | Number of panelists who sensed astringent taste |
| --- | --- |
| Example 3 | 0/20 |
| Example 4 | 0/20 |
| Example 5 | 0/20 |
| Example 6 | 0/20 |
| Example 7 | 0/20 |
| Ferrous sulfate | 20/20 |

As shown in Table 3, the hydrogencarbonic acid-iron-partial hydrolyzates of casein complexes of Example 3–7 has no characteristic astringent taste of iron.

TEST EXAMPLE 3

In a saline phosphate buffer (pH 7.2) containing 6.2 mg/100 g of ascorbic acid and sodium ascorbate as vitamin C, a hydrogencarbonic acid-iron-partial hydrolyzates of casein complex of Example 1 (present invention group 1), a hydrogencarbonic acid-iron-partial hydrolyzates of casein complex of Example 3 (present invention group 2), or ferrous sulfate (control group 1) was dissolved, respectively, to give iron concentration of 20 mg/100 ml. The resultant solutions were heat sterilized at 90° C. for 10 minutes to give test samples. A saline phosphate buffer (pH 7.2) containing 6.2 mg/100 g of ascorbic acid and sodium ascorbate as vitamin C was heat sterilized at 90° C. for 10 minutes to give a test sample (control group 2).

Female Wistar rats of 21 days old just after weaning (Charles River Japan, Inc.) with body weight of 45–50 g were selected and fed for two weeks with an iron deficient feed (iron content of 0.25 mg/100 g of feed, Oriental Yeast Co., Ltd.) to prepare anemia rats with blood hemoglobin concentration of 7 g/100 ml blood or less. The rats were divided in groups each having 8–11 animals and fed for further six weeks with the iron deficient feed together with 1 ml/day of each of the test sample given by gavage. After six weeks of administration of test samples, blood was drawn from tail vein of rats and hemoglobin content was determined with an automatic blood cell counter (Toa Medical Electronics Co., Ltd.). The results are shown in Table 4.

TABLE 4

| | Hemoglobin value (average ± SD) |
|---|---|
| Present invention group 1 | 16.1 ± 1.3 (g/100 ml) |
| Present invention group 2 | 15.8 ± 1.2 |
| Test group 1 | 11.9 ± 0.9 |
| Test group 2 | 4.5 ± 0.5 |

As shown in Table 4, hydrogencarbonic acid-iron-partial hydrolyzates of casein complexes of Examples 1 and 3 exhibited superior therapeutic effect to anemia than those of ferrous sulfate used as tablets.

Comparative Example 1

In a 5% aqueous solution of lactic casein (Dairy Board, New Zealand), sodium hydrogencarbonate was added to adjust the pH at 8.0. In the reaction solution, a protease, papain (W-40., Amano Pharmaceutical Co., Ltd.) was added at a ratio of 10 U/g of casein and the partial hydrolysis was carried out at 65° C. for 30 minutes while maintaining pH at 8.0 by addition of sodium hydroxide. Thereafter, the reaction solution was kept at 85° C. for 20 minutes to inactivate the enzyme activity and terminate the partial hydrolysis. The treated reaction solution was lyophilized to give 3.6 g of hydrolyzates of lactic casein.

Figure 6:
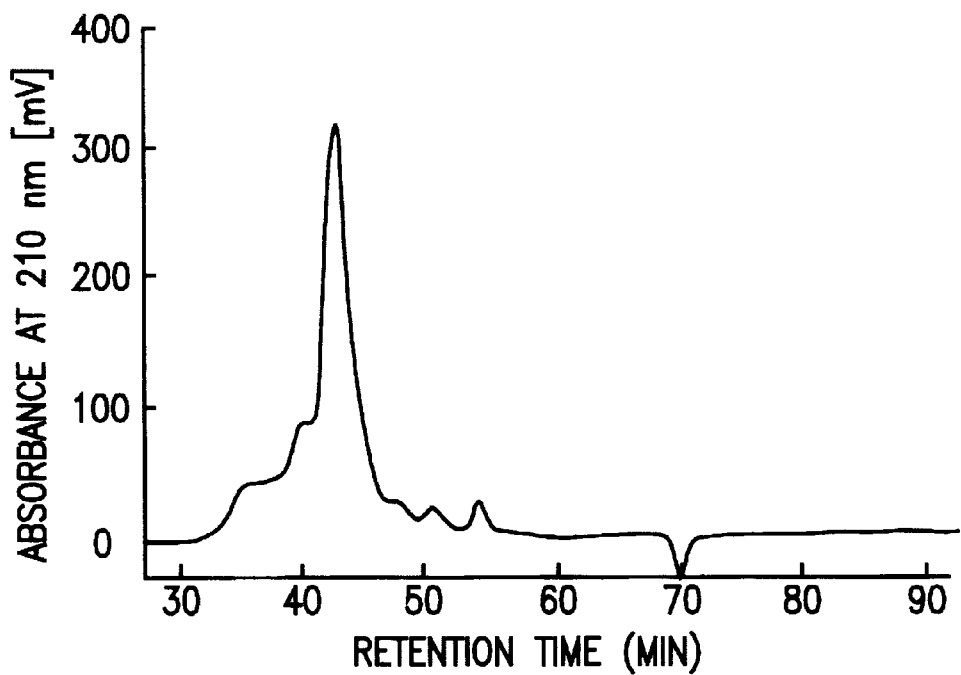
FIG. 6 shows a molecular weight distribution of hydrolyzates of lactic casein obtained by Reference example 1.

The molecular weight distribution of the hydrolyzates of lactic casein was determined in a similar manner with that of Example 3 and the result is shown in FIG. 6. The Figure shows that hydrolyzates of lactic casein having molecular weight of 800–15,000 consists 30% of the total product and the rests have molecular weight of over 15,000.

A hydrogencarbonic acid-iron-hydrolyzates of casein complex was prepared in a similar manner with that of Example 3 using the above mentioned hydrolyzates of lactic casein. The concentration of iron in diffusate of a solution containing hydrogencarbonic acid-iron-hydrolyzates of casein complex was determined in a similar manner with that of Example 3 and no iron was detected. Therefore, all iron is considered to be used as a component of hydrogencarbonic acid-iron-hydrolyzates of casein complex.

A simulated buffer solution prepared by dissolution of the above mentioned hydrogencarbonic acid-iron-partial hydrolyzates of casein complex was diluted to give iron concentration of 3.6 mmol, and was heat sterilized at 90° C. for 10 minutes, and kept at 5° C. observing the formation of precipitates. Formation of precipitates was found after four hours.

Comparative Example 2

In a 5% aqueous solution of lactic casein (Dairy Board, New Zealand), sodium hydrogencarbonate was added to adjust the pH at 7.0. In the reaction solution, a protease, Fishase (Kaken Pharma Co., Ltd.) was added at a rate of 1,000 U/g of casein and caused to partial hydrolysis at 50° C. for five hours while maintaining pH at 7.0 by adding sodium hydroxide. Thereafter, the reaction solution was kept at 85° C. for 20 minutes to inactivate the enzyme activity and terminate the partial hydrolysis. The treated reaction solution was lyophilized to give 2.5 g of hydrolyzates of lactic casein.

Figure 7:
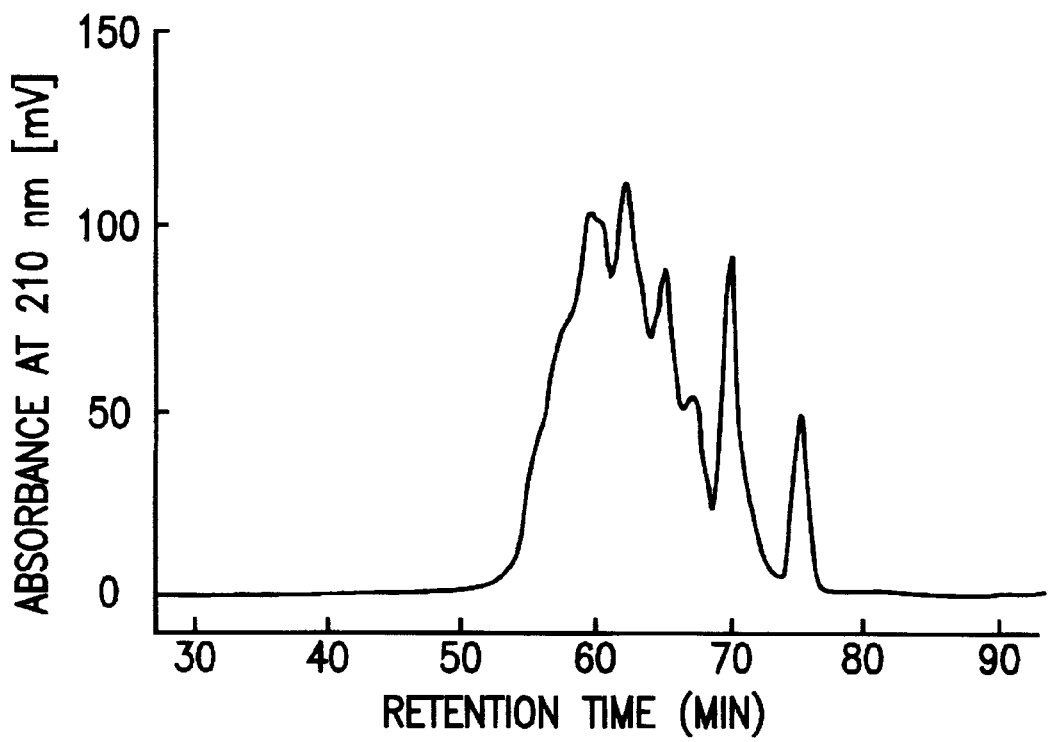
FIG. 7 shows a molecular weight distribution of hydrolyzates of lactic casein obtained by Reference example 2.

The molecular weight distribution of the hydrolyzates of lactic casein was determined in a similar manner with that of Example 3 and the result is shown in FIG. 7. The Figure shows that hydrolyzates of lactic casein having molecular weight of 800–15,000 consists 39% of the total product and the rests have molecular weight of less than 800.

A hydrogencarbonic acid-iron-hydrolyzates of casein complex was prepared in a similar manner with that of Example 3 using the above hydrolyzates of lactic casein. Above mentioned hydrogen-carbonic acid-iron-hydrolyzates of casein complex was diluted with the simulated buffer solution to give iron concentration of 3.6 mmol and was heat sterilized at 90° C. for 10 minutes, then kept at 5° C. observing the formation of precipitates. Formation of precipitates was found after two hours.

As shown by Examples 3–7 and Comparative examples 1–2, it is important to prepare hydrogencarbonic acid-iron-hydrolyzates of casein complex having 55% or less hydrolyzates of casein of molecular weight of over 15,000 and not more than 34% of that of molecular weight of less than 800 to give favorable solubility. If the ratio of partial hydrolyzates of casein with larger or smaller molecular weight goes beyond the above value, the solubility of the hydrogencarbonic acid-iron-hydrolyzates of casein complex decreases.

Applicability for Industrial Use

The carbonic acid- and/or hydrogencarbonic acid-iron-partial hydrolyzates of casein complexes of the present invention have thermoresistance or thermostability, without showing iron characteristic astringent taste after heat sterilization and can exist in aqueous solution, and are useful as raw materials for foods and drinks, medicines and feeds for prevention and treatment of anemia and reinforcement of iron content. Furthermore, as their aqueous solutions do not aggregate or precipitate, and can be handled easily in the production procedure, the loss of the solid mass is very little.

What is claimed is:

1. A carbonic acid- and/or hydrogencarbonic acid-iron-partial hydrolyzate of a casein complexes having following properties of 1) to 4):

1) The complexes containing 1–1,000 atoms of iron and one molecule or more of carbonic acid and/or hydrogencarbonic acid per one molecule of casein prior to the hydrolysis,
   2) the dried powder of the complex dissolves in water to give at least 15% solution,
   3) the aqueous solution shows no precipitation by heating at 90° C. for 10 minutes, and
   4) the solution shows no iron characteristic astringent taste.

2. The carbonic acid- and/or hydrogencarbonic acid-iron-partial hydrolyzate of the casein complex according to claim 1 wherein the partial hydrolyzate of casein is an enzymically hydrolyzed product with a protease having no more than 55% of that of molecular weight of 15,000 or over and no more than 34% of that with molecular weight of less than 800.

3. A process for production of the carbonic acid- and/or hydrogencarbonic acid-iron-partial hydrolyzates of casein complexes according to claim 1 wherein carbonic acid- and/or hydrogencarbonic acid-iron-casein complexes prepared by a reaction of three compounds of carbonic acid and/or hydrogencarbonic acid, iron and casein are partial hydrolyzates with a protease, With a proviso, that the molar concentration of iron ion in preparation of carbonic acid- and/or hydrogencarbonic acid-iron-casein complexes is $\frac{1}{3}$ or less of that of carbonic and hydrogencarbonic acid ions, and molecule number of casein is $1-\frac{1}{1,000}$ of that of iron ion.

4. A process for production of the carbonic acid- and/or hydrogencarbonic acid-iron-partial hydrolyzates of casein complexes according to claim 1 wherein the process is carried out by mixing i) carbonic acid, hydrogencarbonic acid, or carbonic and hydrogencarbonic acids, ii) iron and iii) partial hydrolyzates of casein prepared by partial hydrolysis of casein with a protease to form their complexes, With a proviso, that the molar concentration of iron in the reaction of ii) and iii) is $\frac{1}{3}$ or less of that of carbonic acid and hydrogencarbonic acid ions, and molecule number of partial hydrolyzates of casein is $1-\frac{1}{1,000}$ of that of iron ion calculated as molecule number of casein prior to the partial hydrolysis.

5. A process for production of the carbonic acid- and/or hydrogencarbonic acid-iron-partial hydrolyzates of casein complexes according to claim 3 or 4 wherein the partial hydrolysis is carried out by enzymic hydrolysis of casein with a protease to give hydrolyzed products having no more than 55% of those with molecular weight of 15,000 or more and no more than 34% of those with molecular weight of less than 800.

\* \* \* \* \*